(12) United States Patent
Lanoue

(10) Patent No.: US 6,998,614 B2
(45) Date of Patent: Feb. 14, 2006

(54) HYPERSPECTRAL IMAGING WORKSTATION HAVING VISIBLE/NEAR-INFRARED AND ULTRAVIOLET IMAGE SENSORS

(75) Inventor: Mark Allen Lanoue, Long Beach, MS (US)

(73) Assignee: Institute for Technology Development, Stennis Space Center, MS (US)

( * ) Notice: Subject to any disclaimer, the term of this patent is extended or adjusted under 35 U.S.C. 154(b) by 269 days.

(21) Appl. No.: 10/444,140

(22) Filed: May 23, 2003

(65) Prior Publication Data

US 2004/0232339 A1    Nov. 25, 2004

(51) Int. Cl.
*G01N 21/31* (2006.01)
(52) U.S. Cl. ................................. 250/339.05
(58) Field of Classification Search ........... 250/339.05, 250/339.02
See application file for complete search history.

(56) References Cited

U.S. PATENT DOCUMENTS

| | | | |
|---|---|---|---|
| 5,790,188 A | 8/1998 | Sun | 348/144 |
| 6,211,906 B1 | 4/2001 | Sun | 348/144 |
| 6,222,187 B1 * | 4/2001 | Shivanandan | 250/330 |
| 6,495,818 B1 | 12/2002 | Mao | 250/226 |
| 6,697,155 B1 * | 2/2004 | Dobbs et al. | 356/300 |
| 2003/0123056 A1 * | 7/2003 | Barnes et al. | 356/300 |
| 2004/0135995 A1 * | 7/2004 | Hendrix et al. | 356/237.2 |

* cited by examiner

*Primary Examiner*—Constantine Hannaher
(74) *Attorney, Agent, or Firm*—Crowell & Moring LLP

(57) ABSTRACT

A hyperspectral imaging workstation includes both UV and VNIR sensors together in a single enclosure. Each sensor captures an image of a target or specimen, resulting in respective UV and VNIR data sets which are then merged into a single hyperspectral data set that includes a highly correlated contiguous spectral bands throughout a range of from 200 to 1000 nanometers.

14 Claims, 3 Drawing Sheets

HYPERSPECTRAL IMAGING WORKSTATION HAVING VISIBLE/NEAR-INFRARED AND ULTRAVIOLET IMAGE SENSORS

BACKGROUND OF THE INVENTION

The invention is directed to a high spatial and spectral resolution hyperspectral imaging workstation that is capable of capturing hyperspectral imaging in both the ultraviolet (UV) and visible and near-infrared range ("VNIR") portions of the electromagnetic spectrum. In particular, the hyperspectral imaging workstation according to the invention includes sensors for acquiring separate image data sets in the 200–400 nanometer range (UV) and in the 400–1,000 nanometer (VNIR). The system according to the invention is capable of performing wavelength specific feature extraction and other spectral comparisons on the resulting data sets.

Hyperspectral imaging systems in general are known, and have been used for a diverse range of remote sensing and other analytical techniques, such as is disclosed, for example, in U.S. Pat. No. 5,790,188 and the related U.S. Pat. No. 6,211,906. Hyperspectral imaging has also been used in conjunction with microscopic optical systems, such as disclosed, for example, in U.S. Pat. No. 6,495,818. In such systems, radiation reflected by or emanating from a target or specimen is detected in a large number of narrow contiguous spectral bands, producing a data set which is distributed not only spatially, but spectrally as well. That is, for each pixel within an image of the target, information is recorded in each of the spectral bands, thereby producing a three-dimensional hyperspectral image cube, in which spectral information for each pixel is distributed across a spectral axis perpendicular to the spatial axes.

Previously known hyperspectral imaging workstations, such as the model UV 100E, VNIR 100E, and SWIR 100E provided, for example, by ProVision Technologies of Stennis Space Center, MS, have been capable of capturing hyperspectral image data, for example, within the UV range, from 200 to 400 nanometers, the VNIR range, from 400 to 1,000 nanometers, and the SWIR range from 900 to 2400 nanometers. However, heretofore, no such workstation has been available which produces highly correlated contiguous spectral band data throughout a range from 200 to 1,000 nanometers; that is, including not only the VNIR range, but the UV range as well.

Accordingly, one object of the present invention is to provide a hyperspectral imaging workstation that includes sensors for acquiring separate image data sets in both the ultraviolet and the visible and near-infrared ranges of the electromagnetic spectrum.

Another object of the present invention is to provide a hyperspectral imaging workstation that is capable of providing hyperspectral and imaging data for a large number of contiguous spectral bands throughout a range of from 200 to 1,000 nanometers.

These and other objects and advantages are achieved by the hyperspectral imaging apparatus according to the present invention which includes both UV and VNIR sensors together in a single enclosure. Each sensor captures an image of the target or specimen, resulting in respective UV and VNIR data sets which are then merged into a single hyperspectral data set which includes highly correlated contiguous spectral bands throughout a range of from 200 to 1,000 nanometers, or are provided seperately per end-user software settings.

The system according to the invention permits the detection and analysis of small nuances and information that are otherwise undetectable in systems that use a wide swath filter. Also, the entire range, from 200 to 1,000 nanometers can be used to identify pertinent wavelengths across a wide yet largely defined region of the electromagnetic spectrum for a wide variety of applications that can be programmed as algorithms within the system, or used to develop derivative systems. For example, certain inks that need to be defined when looking at genuine versus counterfeit documents may show regions of interest in both the UV and IR ranges, while others may be found within the visible portion of the electromagnetic spectrum.

Furthermore, the combination of a controlled lighting environment and the ability to use National Institute of Standards and Technology (NIST) traceable diffuse reflectance standards with each scan insures consistent and reproducible results.

The system according to the invention is run by a programmed data processor/software or computer that triggers the lights, hyperspectral cameras and computerized translation stage to acquire and process a fully explorable hyperspectral data cube. The translation stage moves beneath the sensors, allowing the line slit on the optical devices to acquire the entire target. The latter process is performed separately by both cameras, within separate ranges. Thereafter, the resulting data sets are combined in a known manner or provided separately per end-user software settings.

Other objects, advantages and novel features of the present invention will become apparent from the following detailed description of the invention when considered in conjunction with the accompanying drawings.

DETAILED DESCRIPTION OF THE DRAWINGS

Figure 1:
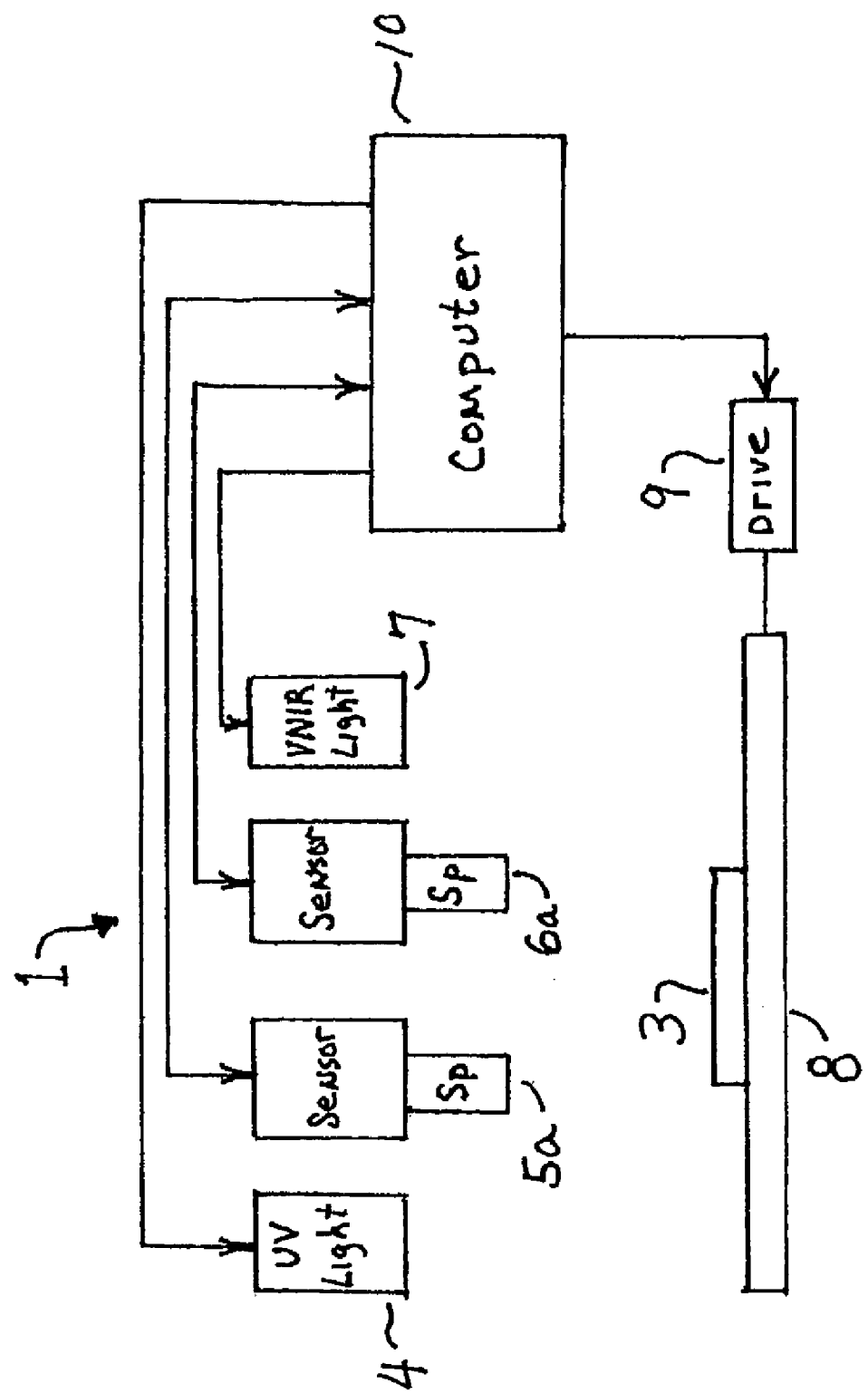
FIG. 1 is a conceptual block diagram which shows the general configuration of the hyperspectral imaging workstation according to the invention.
Figure 2:
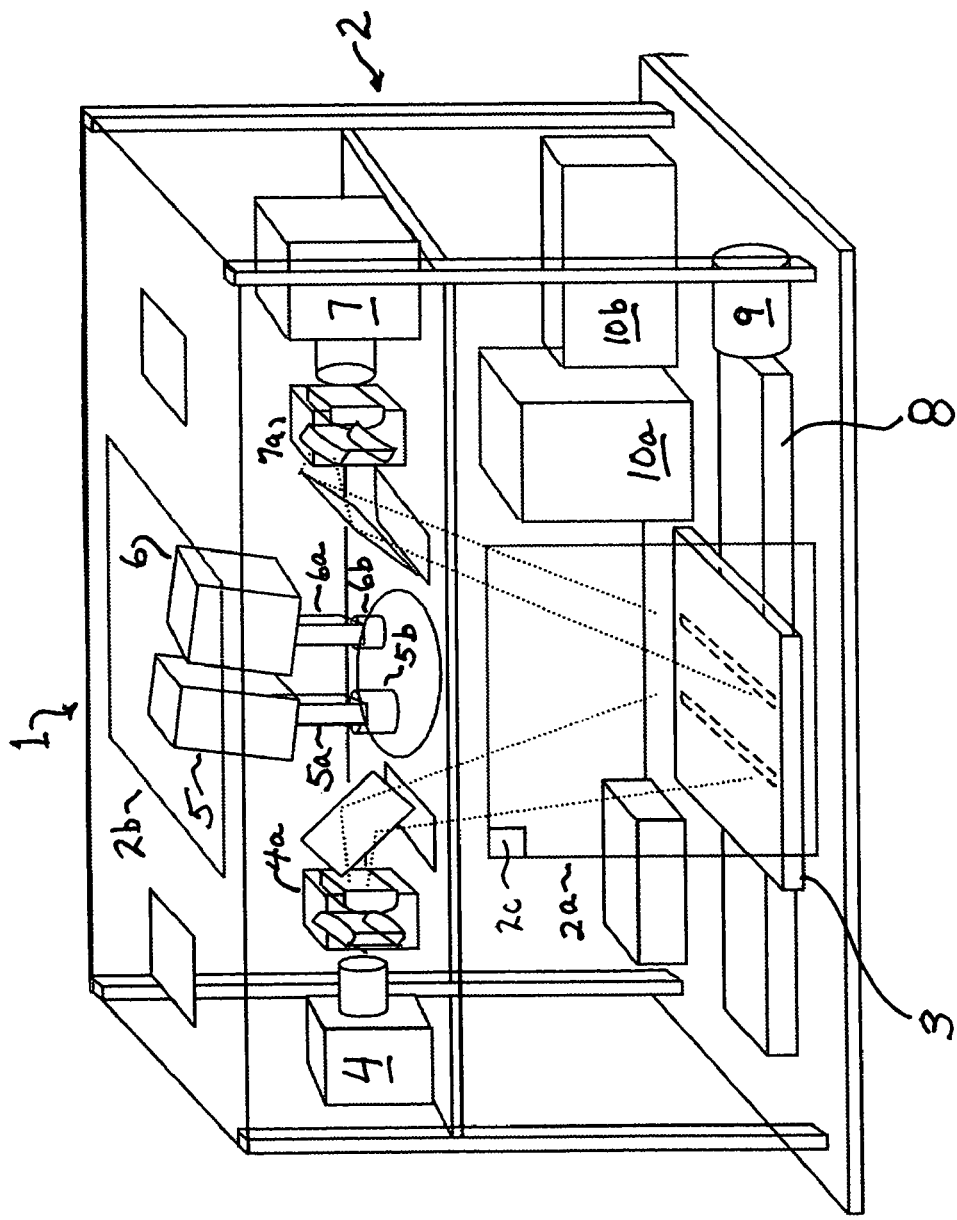
FIG. 2 is a schematic perspective view of the workstation of FIG. 1, showing additional construction details.

FIGS. 1 and 2 show, respectively, a conceptual block diagram, and a schematic perspective view of the hyperspectral imaging workstation 1 according to the invention. As can be seen in FIG. 2 in particular, the entire workstation is contained within an enclosure 2 having doors 2a and 2b for gaining access to a platform 3 for supporting a specimen, and to the optical components of the workstation.

As best seen in FIG. 1, the workstation according to the invention includes a UV light source 4 for illuminating a specimen supported on the platform 3, and a sensor 5 for detecting reflected electromagnetic radiation within the ultraviolet range of 200 to 400 nanometers. In addition, a VNIR light source 7 is also provided, for illuminating the specimen with electromagnetic radiation in the VNIR range, from 400 to 1,000 nanometers, and a second sensor 6 is provided for detecting reflected electromagnetic radiation in the VNIR range. Each of the respective sensors 5,6 has associated with it a spectrograph 5a,6a that disperses reflected light within the wavelength range of the sensor with which it is associated, into small contiguous wavelengths/bands.

For the purpose of scanning a specimen supported on the platform 3, a translation stage 8 is driven by a drive element 9, a computer 10 controls the operation of the respective UV and VNIR light sources 4,7, as well as the drive element 9.

The components illustrated in block form in FIG. 1 are shown in somewhat greater detail in the schematic illustration in FIG. 2. Each of the respective UV and VNIR light sources 4,7 has associated therewith a set of spherical lenses 4a,7a which evenly disperse a light beam across a target supported on the platform 3, under the respective imaging slits and lens systems of the UV and VNIR hyperspectral imagers 5 and 6. The ultraviolet light source may be, for example, either a deuterium or xenon source, which emits ultraviolet radiation down to 200 nanometers at a quantum efficiency of approximately fifty percent (50%) at 200 nanometers and twenty percent (20%) at 400 nanometers. Such illumination sources or lamps are commercially available, for example, from Oriel Instruments of Stratford, Conn. The VNIR light source, on the other hand may be a halogen source, such as is also available from Oriel Instruments. The latter emits color balanced radiation from 400 nanometers to 1,000 nanometers.

The respective UV and VNIR sensors 5,6 are each sensitive to the specific optics (that is, the spectrograph systems or dispersion optics discussed below) associated therewith. Suitable commercially available off-the-shelf sensors may be used for this purpose. For example, the UV sensor 5 may be a Micromax ultraviolet sensor with UNICHROME coating, such as is available from Roper-Scientific, while the VNIR sensor may be, for example, in the form of a COOKE Sensi-Cam QE available from the COOKE Corporation, Auburn Hills, Mich. The UV sensor is sensitive within the range of 200 to 1,100 nanometers, while the VNIR sensor is sensitive within the range from 280 to 1,000 nanometers. It should be noted in this regard that while the sensitivity ranges of the respective sensors themselves are largely overlapping, the actual range of reflected radiation sensed by each of the respective sensors is determined by the dispersion optics (spectrographs) associated therewith.

Figure 3:
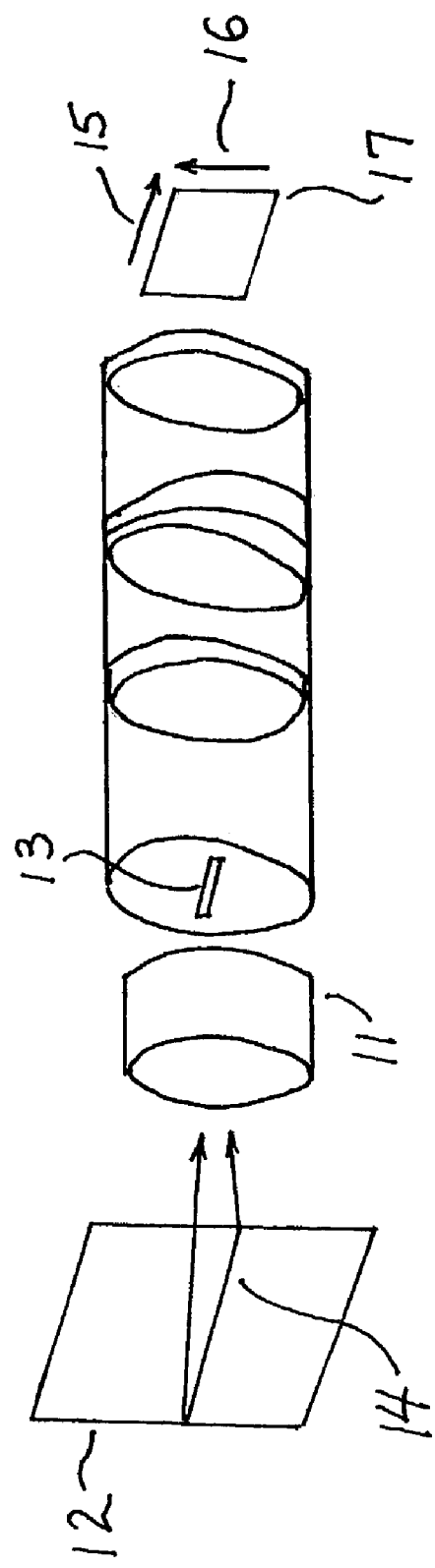
FIG. 3 is a partially broken away perspective view of the spectrograph instrument of FIGS. 1 and 2.

The spectrographs (dispersion optics) 5a,6a are positioned in front of each of the sensors 5,6 and behind collection lenses 5b,6b. The details of the spectrographs are shown in FIG. 3, in which an objective lens 11 focuses an image from a specimen 12 on an entrance slit 13 that defines a transverse image line 14 on the specimen. Light from the image line 14 is passed through the slit 13, as well as through a series of lenses, prisms and gratings within the body of the spectrograph, and is projected onto a sensing device which includes a matrix of sensors in a two-dimensional planar array defined by a spatial axis 15 parallel to the line image, and a spectral axis 16 perpendicular to the spatial axis 15. Light emanating from the line image on the target is focused along the spatial axis 15 of the sensor 17, while for each pixel, on the spatial axis, light from the line image is spread spectrally along the spectral axis. As the specimen, which is supported on the specimen platform 3 in FIGS. 1 and 2 is translated along a direction perpendicular to the line image, a three-dimensional data set is derived, which includes two-dimensional spatial information ("x" and "y" dimensions) and spectral information ("z" dimension) as well.

The spectrograph used in the VNIR range may be a commercial off-the-shelf system that disperses wavelengths between 400 and 1,000 nanometers into small contiguous wavelengths/bands, as noted previously. Such a system is available, for example, from Spectral Imaging Limited of Oulu, Finland (model VIOE). The ultraviolet spectrograph 5a has construction similar to that of the VNIR spectrograph 6a and functions in essentially the same manner, as is illustrated in FIG. 3, and disperses wavelengths from 200 to 400 nanometers. Although the spectrograph is being used for the 200 to 400 nanometer range for this particular configuration, it actually disperses energy out beyond the 600 nanometer range. However, this added range provides higher quantum efficiency at the 400 nanometer wavelength where the VNIR system takes over. The spectrograph disperses wavelength energy onto the CCD in the same fashion as the VNIR spectrograph. The spectrograph is attached to the front of a UV sensitive camera via a specific camera mount (c-mount, f-mount, s-mount, etc.) and a collection lens is fitted to the front of the spectrograph in the same fashion allowing the collection of wavelengths in the "z" dimension, and spatial information in the "x" and "y" dimension. The spatial dimension is captured one line at a time and the spectral dimension contains all wavelengths for that given line. The data cube provided in this wavelength range is then constructed line-by-line via a push-broom scanning method using a linear stage and programmed software.

It should be noted that the spectrographs described in detail herein are cited only by way of example, and that the use of other types and configurations of spectrographs are also within the scope of the invention.

The translation stage 8 shown in FIGS. 1 and 2 has a rotary motor 9 with a rotary encoder for speed and rough positioning. The stage also has a linear encoder for precise positioning. Such a translation stage is available, for example, from Cross Automation, of Belmont, N.C., and associated actuators are available Galil Motion Control, Rocklin, Calif.

The light excluding enclosure 2 is depicted schematically in FIG. 2, and includes access doors 2a and 2b for gaining access to the specimen and to the sensors. In FIG. 2, the computer 10 of FIG. 1 is shown as broken into two separate components 10a and 10b for controlling the translation stage and the cameras and lights respectively. It is of course apparent that the computer may also be situated outside the enclosure 2.

In operation, a specific is first placed on the support platform 3, via access door 2a in FIG. 2, with the imaging platform positioned to the center of the access door by the computer 10. (Opening the access door 2a automatically disables the ultraviolet light source via a cutoff switch 2c, in order to prevent the operator from being exposed to ultraviolet light.) Once the target platform is centered with the access door, the end user places onto the platform a specimen which is to be scanned. When the access door 2a is closed, the imaging platform is positioned for the start of a scan under the first hyperspectral imager 6, which is at the same time activated by the computer, together with the VNIR light source 7 which disperses a narrow light beam evenly across the target under the imaging slit and lens of the VNIR hyperspectral imager 6. The computer then causes the driver motor 9 to move the linear translation stage 8 under the hyperspectral imager until the entire platform is imaged. The linear translation stage is then repositioned by the computer to allow the ultraviolet hyperspectral imager 5 to be engaged along with the ultraviolet light source 4, and the specimen is once again scanned in the same manner.

The result of these scanning operations is the generation of first and second processed/calibrated hyperspectral image data cubes containing respective ultraviolet and VNIR data sets. Both data sets can then be subsampled and combined via a MATRIX code algorithm, using commercial off-the-shelf image processing packages. (A MATRIX code is a pattern recognition routine known to those skilled in the art, which can identify a target or be used to quantify data produced from a target.) The ultimate resulting data set is that of a high resolution hyperspectral data set that has highly correlated contiguous spectral bands throughout a range from 200 to 1,000 nanometers.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A hyperspectral imaging device, comprising:
   a light excluding enclosure;
   a platform for supporting a specimen within said enclosure;
   a first light source which emits radiation throughout a VNIR portion of the electromagnetic spectrum, and is positioned within said enclosure to illuminate a specimen on said platform;
   a first hyperspectral imager for sensing VNIR radiation reflected from a specimen on said platform, in a plurality of contiguous spectral bands throughout said VNIR portion of the electromagnetic spectrum;
   a second light source which emits radiation throughout a UV portion of the electromagnetic spectrum, and is positioned within said enclosure to illuminate a specimen on said platform;
   a second hyperspectral imager for sensing UV radiation reflected from a specimen on said platform, in a plurality of contiguous spectral bands through said UV portion of the electromagnetic spectrum; and
   a translation stage for moving the specimen platform relation to each of said first and second hyperspectral imagers.

2. The hyperspectral imaging device according to claim 1, further comprising means for combining hyperspectral image data sets generated by said first and second hyperspectral imagers.

3. The hyperspectral imaging device according to claim 2, wherein said means for combining hyperspectral image data sets comprises a programmed computer that processes a fully explorable hyperspectral data cube.

4. The hyperspectral imaging device according to claim 1, wherein:
   said first light source emits VNIR radiation throughout a range from 400 to 1000 nanometers; and
   said second light source emits UV radiation throughout a range of from 200 to 400 nanometers.

5. The hyperspectral imaging device according to claim 4, wherein:
   said first hyperspectral imager comprises a first CCD array that is responsive to VNIR radiation throughout said range of 400 to 1000 nanometers, and a device which disperses said VNIR radiation from 400 to 1000 nanometers along a first axis of said first CCD array; and
   said second hyperspectral imager comprises a second CCD array that is responsive to UV radiation throughout said range of 200 to 400 nanometers, and a device which disperses said UV radiation from 200 to 400 nanometers across a first axis of said second CCD array.

6. The hyperspectral imaging device according to claim 1, wherein:
   said first and second light sources illuminate the specimen with an elongate beam of light that extends transversely to a direction of movement of said specimen on said platform;
   each of said first and second hyperspectral imagers comprises a two-dimensional planar array of sensors, having a spatial axis that corresponds to an axis transverse to a direction of movement of said specimen on said platform, and a spectral axis which corresponds to said plurality of contiguous hyperspectral bands.

7. The hyperspectral imaging device according to claim 6, wherein said first and second hyperspectral imagers disperse said reflected radiation through the respective UV and VNIR portions of the electromagnetic spectrum, along said spectral axis of said respective planar arrays.

8. The hyperspectral imaging device according to claim 1, wherein:
   operation of the light sources, imagers and translation stage is controlled by a programmed data processor; and
   said first light source and first imager are operated alternately with said second light source and second imager;
   whereby when one of said light sources is activated, the other is not.

9. The hyperspectral imaging device according to claim 1, wherein:
   said light excluding enclosure further comprises an access door for providing access to the imaging platform; and
   a cutoff switch is provided to automatically disable the second light source when the access door is open.

10. A method for acquiring hyperspectral image data characterizing a specimen, said method comprising:
    supporting said specimen in a light excluding enclosure;
    sequentially illuminating said specimen with VNIR light in a VNIR portion of the electromagnetic spectrum, and UV light in a UV portion thereof;
    during illumination of said specimen by UV light, detecting light reflected from said specimen using a first hyperspectral imager, to acquire a first set of hyperspectral image data in a plurality of contiguous spectral bands throughout said UV portion of the electromagnetic spectrum;
    during illumination of said specimen by VNIR light, detecting light reflected from said specimen using a second hyperspectral imager, to acquire a second set of hyperspectral image data in a plurality of contiguous spectral bands throughout said VNIR portion of the electromagnetic spectrum;
    combining said first and second sets of hyperspectral image data.

11. The method according to claim 10, wherein said combining step comprises using a MATRIX code to define pixel size and orientation.

12. The method according to claim 11, further comprising:
    moving said specimen along a translation direction through an imaging position during each of said illumination steps; and
    detecting radiation reflected from said specimen along an axis transverse to said translation direction during said moving step.

13. The method according to claim 11, wherein said combining process is performed by a programmed computer that processes a fully explorable hyperspectral cube.

14. The method according to claim 10, further comprising:
moving said specimen along a translation direction through an imaging position during each of said illumination steps; and
detecting radiation reflected from said specimen along an axis transverse to said translation direction during said moving step.

* * * * *